United States Patent [19]

Smith

[11] Patent Number: 4,507,283

[45] Date of Patent: Mar. 26, 1985

[54] PHARMACOLOGICALLY ACTIVE COMPOUNDS

[75] Inventor: Richard A. G. Smith, Reigate, England

[73] Assignee: Beecham Group p.l.c., England

[21] Appl. No.: 482,136

[22] Filed: Apr. 5, 1983

[30] Foreign Application Priority Data

Apr. 7, 1982 [GB] United Kingdom ............... 8210262

[51] Int. Cl.$^3$ ..................... A61K 37/48; C12N 9/96; C12N 9/48; C12N 9/70; C12N 9/68

[52] U.S. Cl. ..................................... 424/94; 435/188; 435/212; 435/216; 435/217

[58] Field of Search ............... 435/212, 216, 188, 217; 424/94

[56] References Cited

U.S. PATENT DOCUMENTS 4,285,932 8/1981 Smith .................................... 424/94

FOREIGN PATENT DOCUMENTS 0009879 4/1980 European Pat. Off. .
0028489 5/1981 European Pat. Off. .

OTHER PUBLICATIONS

Chem. Abstracts, vol. 71, No. 3, (1969), p. 30, No. 9835z.
Chem. Abstracts, vol. 75, No. 3, (1971), p. 50, No. 1543u.
Chem. Abstracts, vol. 82, No. 17, (1975), p. 93, No. 10697c.

Primary Examiner—Lionel M. Shapiro
Attorney, Agent, or Firm—Jacobs & Jacobs

[57] ABSTRACT

A derivative of streptokinase-human plasminogen activator complex, in which the active catalytic site essential for fibrinolytic activity is blocked by a 2- or 4-aminobenzoyl group, is useful in treating venous thrombosis.

The blocking group is removable by hydrolysis such that the first order rate is in the range $0.7 \times 10^{-5} \text{sec}^{-1}$ to $2.5 \times 10^{-5} \text{sec}^{-1}$ in isotonic aqueous media at pH 7.4 at 37° C.

16 Claims, 2 Drawing Figures

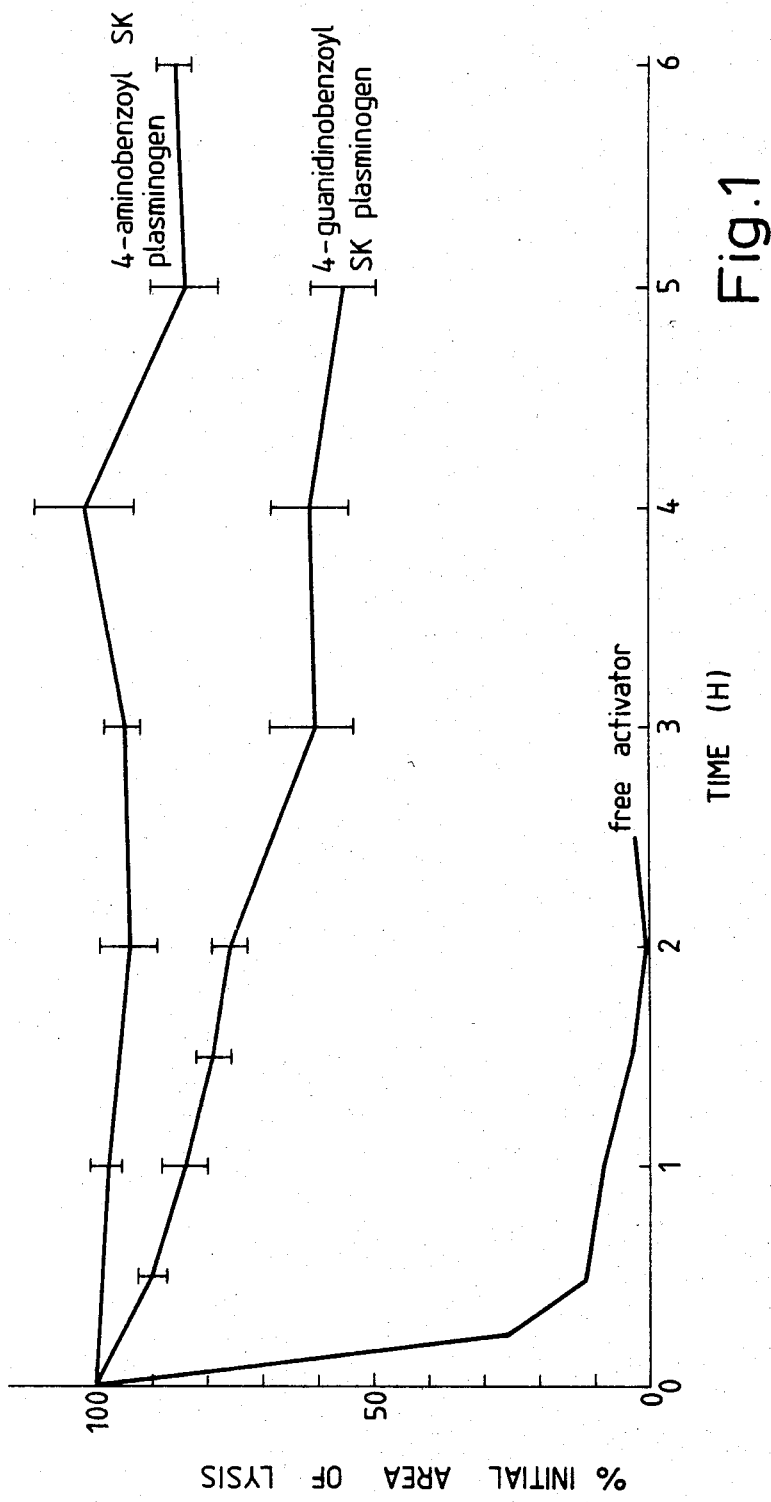

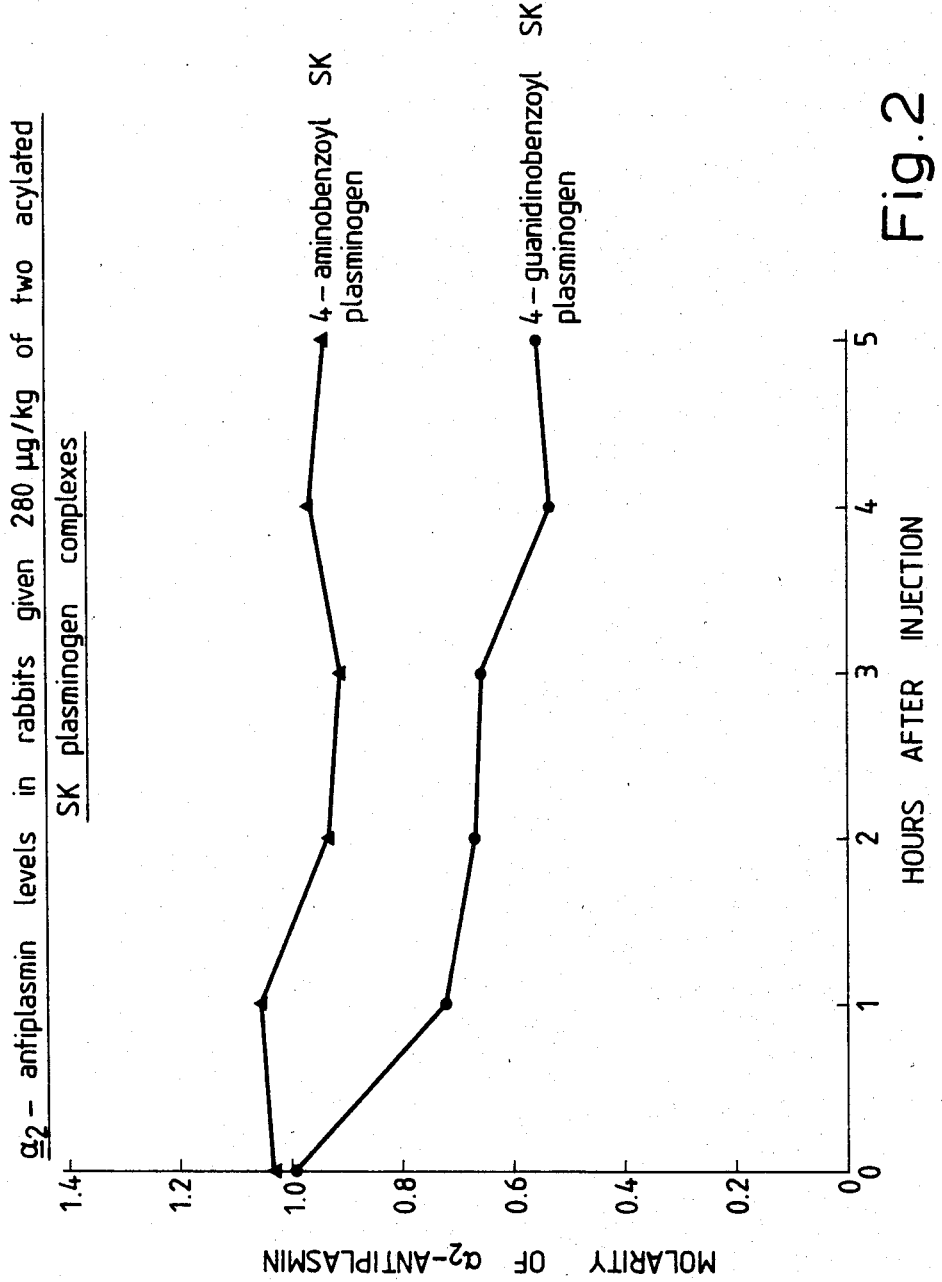

PHARMACOLOGICALLY ACTIVE COMPOUNDS

This invention relates to enzyme derivatives for use in the treatment of venous thrombosis.

European Published patent application No. 0,009,879 discloses derivatives of in vivo fibrinolytic enzymes which are useful therapeutic agents for treating venous thrombosis. The derivatives are characterised by the active catalytic site on the enzymes being blocked by a group which is removable by hydrolysis such that the pseudo-first order rate constant for hydrolysis is in the range $10^{-6}$ sec$^{-1}$ to $10^{-3}$ sec$^{-1}$. Suitable blocking groups disclosed in the published application are acyl groups, particularly optionally substituted benzoyl groups.

It has now been found that a small group of blocked enzymes within the broad scope of the above published application but not specifically disclosed therein, have surprising slow physiological clearance rates and prolonged in vivo stability which makes them particularly useful for the treatment of mature venous thrombi. This activity is coupled with a very slow depletion of $\alpha_2$-antiplasmin.

Accordingly, the invention provides a derivative of streptokinase-human plasminogen activator complex in which the active catalytic site essential for fibrinolytic activity is blocked by a 2- or 4-aminobenzoyl group which is optionally substituted in the aromatic ring by an electron donating moiety, the group being removable by hydrolysis such that the first order rate constant for hydrolysis of the derivative is in the range $0.7 \times 10^{-5}$ sec$^{-1}$ to $2.5 \times 10^{-5}$ sec$^{-1}$ in isotonic aqueous media at pH 7.4 at 37° C.

Preferably the aminobenzoyl group is unsubstituted in the aromatic ring.

When the aromatic ring is substituted, preferred electron donating moieties include $C_{1-6}$ alkyl, $C_{1-6}$ alkoxy or $C_{1-6}$ alkenyl, particularly $C_{1-6}$ alkyl.

The preferred range of first order rate constant is from $1 \times 10^{-5}$ sec$^{-1}$ to $2 \times 10^{-5}$ sec$^{-1}$.

Preferred derivatives of this invention include the following:

4-aminobenzoyl streptokinase-plasminogen activator complex;

2-aminobenzoyl streptokinase-plasminogen activator complex;

2- or 4-amino-3-methylbenzoyl streptokinase plasminogen activator complex.

The pseudo-first order rate constant is determined by hydrolysing the derivative under physiological conditions, ie in isotonic aqueous media at pH 7.4 and at 37° C. At regular intervals aliquots are withdrawn and incubated with a chromogenic or fluorgenic protease substrate such as S-2251 (H-D-Val-Leu-Lys-p-nitroanilide 2HCl) and the rate of conversion of the substrate measured.

The hydrolysis is followed until such time as the rate of conversion of substrate reaches a maximum. The rate constant k is then calculated by plotting:

$$\log_e(1 - A_t/A_{max}) \text{ against } t$$

where $A_{max}$ the maximum rate at which an aliquot converts substrate and $A_t$ is the rate at which an aliquot converts substrate at time t.

The derivative of the invention may be prepared by reacting streptokinase-plasminogen activator complex with a blocking agent

AB in which A is a locating group which locates the agent in the catalytic site, and B is a 2- or 4-aminobenzoyl group optionally substituted in the aromatic ring by an electron donating moiety, preferably a $C_{1-6}$ alkyl, $C_{1-6}$ alkoxy or $C_{1-6}$ alkenyl group.

Examples of the group A include 4-amidinophenyl and 4-acetamidinophenyl or structurally similar substituted phenyl groups containing a positively charged moiety in the 3- or 4-position.

Preferred agents AB are 4-amidinophenyl-4'-aminobenzoate, 4-amidinophenyl-2'-aminobenzoate, 4-amidinophenyl-2'-amino-3'-methylbenzoate, and 4-amidinophenyl-4'-amino-3'-methylbenzoate.

The blocking reactions are preferably carried out in aqueous media at a pH range which is not detrimental to the enzyme, blocking agent or product, eg between pH 4 and 8 and preferably at a pH in the range 5.0 to 7.5.

The reaction is generally carried out using a molar excess of blocking agent, but equi-molar equivalents may also be employed. It is also preferred to carry out the reaction in dilute solution, ie less than $10^{-3}$ molar with respect to enzyme and less than $10^{-2}$ molar with respect to blocking agent. Generally the reaction will not be carried out in a solution where the concentration of enzyme or blocking agent is less than $10^{-7}$ molar.

The blocking reaction should be carried out at moderate temperatures, ie room temperature or below, and more particularly less then 10° C. but greater than the freezing point of the reaction medium.

The blocking agent

AB wherein A is 4-amidinophenyl, may be prepared by reacting 4-amidinophenol with an N-protected 2- or 4-aminobenzoic acid, optionally substituted in the aromatic ring by an electron donating moiety, and subsequently deprotecting the resulting product. A suitable protecting group is the tertiary-butoxy-carbonyl (BOC) group. The reaction is preferably carried out in a tertiary organic base, such as pyridine, and in the presence of a condensation promoting agent such as dicyclohexyl carbodiimide. If desired, the condensation reaction may also be carried out without prior protection of the amino group.

The N-protection of the aminobenzoic acid material is preferably carried out by treating the material with ditertiary butyl dicarbonate. The de-protection of the product is suitably carried out by treating the product with trifluoroacetic acid (TFA), preferably at room temperature.

The derivative of this invention is preferably administered as a pharmaceutical compostion.

Accordingly the present invention also provides a pharmaceutical composition comprising the derivative of the invention in combination with a pharmaceutically acceptable carrier.

The compositions according to the invention may be formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubilising agent to keep the derivative in solution and a local anaesthetic such as lignocaine to ease pain at the site of injection. Generally, the enzyme derivative will be supplied in unit dosage form for example as a dry powder or water free concentrate in a hermetically sealed container such as an ampoule or sachette indicating the quantity of enzyme in activity units, as well as an indication of the time within which the free enzyme will be liberated. Where the derivative is to be administered by infusion, the derivative will be dispensed with an infusion bottle containing sterile pharmaceutical grade "Water for Injection". Where the derivative is to be administered by injection the derivative is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and position and size of the clot. The precise dose to be employed and mode of administration must per force in view of the nature of the complaint be decided according to the circumstances by the physician supervising treatment. However, in general, a patient being treated for a mature thrombus will generally receive a daily dose of from 0.25 to 2.0 mg/kg$^{-1}$ of body weight either by injection in up to five doses or by infusion.

Accordingly, in a further aspect of the invention there is provided a method of treating venous thrombosis, which comprises administering to the sufferer an effective non-toxic amount of the derivative of the invention.

The following Examples illustrate the invention.

Examples 1 to 4 illustrate the preparation of blocking agents and Examples 5 to 8 illustrate the preparation of derivatives of the invention.

EXAMPLE 1

(a) Preparation of 4-amidinophenyl-4'-aminobenzoic acid trifluoroacetate (method 1)

(i) N-(t-BOC)-4-aminobenzoic acid

4-Aminobenzoic acid (4.1 g) was dissolved in DMF (25 ml) and 1M NaOH (30 ml) added. To this was added ditertiarybutyl dicarbonate (8 ml) and the reaction allowed to proceed for 45 h at room temperature. The solvent was removed by rotary-evaporation and the solid dissolved in ethyl acetate/water ca 1:2 (total 300 ml). 20% Citric acid (150 ml) was added and the organic layer washed with 10% citric acid (5 vols), saturated NaCl (2 vols) and water (2 vols). After filtering off a small amount of solid, the product was precipitated with pet. ether 40/60, filtered and dried. It was redissolved in ethanol (min. volume) and 0.1% citric acid added to the cloud point. After 16 h at 5° C., crystals of the title compound were recovered.

Yield: 3.9 g (55%) mp 197° C. (decomp.).

$^1$HNMR 9.72 (1H, s), 7.70 (4H, AB), 1.50 (9H, s).

(ii) N-(t-BOC)-4-aminobenzoic acid 4'-amidinophenyl ester

BOC-4-Aminobenzoic acid (1.51 g) and 4-amidinophenol (1.09 g) were dissolved in dry pyridine (25 ml). DCCI (1.34 g) was added and the mixture stirred at room temperature for 3 days. After cooling at 4° C., the precipitate was filtered and washed with pyridine. Dicyclohexylurea was removed by extraction with CHCl$_3$ (150 ml for 0.5 h, then 250 ml for 16 h). Yield of crude title product: 1.90 g (77%).

$^1$HNMR 9.90 (1H, s), 9.40 (4H, d), 7.5–8.2 (8H, aromatic), 1.50 (9H, s).

(iii) 4-amidinophenyl-4'-aminobenzoic acid trifluoroacetate

4-[N-(t-BOC)]-aminobenzoyl-4'-amidinophenol (1.90 g) was treated with TFA (5 ml) for 1 h at room temperature. Excess TFA was removed by rotary-evaporation and the residue dried in vacuo. The product was triturated with ether, filtered and redissolved in hot MeOH. Ether was added to the cloud point and the mixture cooled at −18° C. The precipitate (0.2 g) was filtered off and discarded. The product was precipitated with a large excess of pet. ether 40/60 and dried. Yield: 1.41 g (TFA salt, 55%). 0.5 g recrystallised from isopropanol/pet. ether 40/60.

Yield 250 mg. mp 208°–211° C.

$^1$HNMR 9.30 (4H, broad s), 7.4–8.0 (6H, aromatic), 6.63 (2H, d), 6.23 (2H, broad s).

(b) Preparation of 4-amidinophenyl-4'-aminobenzoate hydrochloride (method 2)

4-Aminobenzoic acid (690 mg=5 mmoles) and 4-amidinophenol hydrochloride (860 mgs=5 mmoles) were dissolved in pyridine (10 mls) with stirring and cooled in ice. Dicyclohexylcarbodiimide (1.13 gms=5.5 mmoles) was added in pyridine (7 mls) and reaction mixture was stirred for 16 hours at room temperature. The reaction was cooled to −18° C., filtered and the precipitate washed with cold pyridine and dry diethyl ether. The solid was stirred at room temperature with chloroform (2×400 mls) for 2 hours and the remaining solid was obtained by filtration to give the required compound, (670 mgs, 46%). Further purification could be effected from methanol/diethyl ether to yield white crystals (Mp 222°–225° C.).

$^1$H nmr: (d$^6$DMSO) 9.50 (s, 4H,

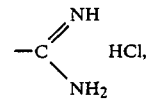

8.00, 7.84, 7.48, 6.68 (all d, 2H, aromatic AB systems), 6.32 (s, 2H, NH$_2$).

(c) Preparation of 4-amidinophenyl-2'-aminobenzoate 4-toluenesulphonate (i) 4N(Benzyloxycarbonyl)amidinophenyl-2'-aminobenzoate Isatoic anhydride (97%, 340 mgs, 2 mmoles) was heated in sodium dried dioxan AR (10 mls) with (N-benzyloxycarbonyl)-4-amidinophenol (540 mgs 2 mmoles) and powdered sodium hydroxide (4 mgs). The temperature was raised slowly to 100° C. and effervescence occurred above 750° C. Heating was continued until effervescence ceased after 1.5 hours, the solution was allowed to cool and added to water (100 mls). A solid crystallised out and this was recrystallised from methanol (50 mls) to yield the desired material (340 mgs, 44%, mp 162°–164° C.);

¹H nmr (CDCl₃): 8.13–7.13 (m, 13H, aromatics), 6.70 (m,

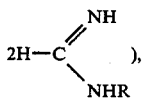

5.72 (s, broad, 2H, NH₂), 5.18 (s, 2H, OCH₂Ph).

(ii) 4-Amidinophenyl-2'-aminobenzoate 4-toluene sulphonate

Palladium black (210 mgs) was stirred under nitrogen in a solution of formic acid in methanol (4.4%). N-(benzyloxycarbonyl)-4-amidinophenyl-2'-aminobenzoate (240 mgs, 0.62 mmoles) was added to the solution after it had been dissolved by heating in 45 mls of the same solution. The mixture was stirred for 2 hours, filtered and the palladium black washed with methanol and water. The filtrate was evaporated in vacuo. The residue was dissolved in methanol and 4-toluene sulphonic acid monohydrate (120 mgs, 0.63 mmoles) was added to it. The solution was heated and diethyl ether added until cloudpoint. Cooling effected crystallisation to yield the product (60 mgs, 22%), mp 209°–213.5° C., $C_{21}H_{31}N_3O_5S$ required C, 59.0; H, 5.0; N. 9.8; S, 7.5%. Found C, 58.7; H, 4.8; N, 9.6; S, 7.0%.

¹H nmr (d⁶DMSO): 9.17 (s, broad,

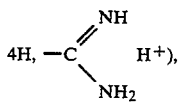

8.0–6.5 (m, 14H, aromatics), 2.30 (s, 3H,

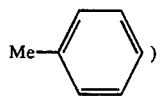

Impurity 0.5H at 3.28.

EXAMPLE 2

Preparation of 4-amidinophenyl-4'-amino-3'-methyl benzoate hydrochloride 4-amino 3-methylbenzoic acid (1.51 g, 10 mmol) and 4-amidinophenol HCl (1.72 g, 10 mmol) were dissolved in dry pyridine (20 ml) and dicyclohexylcarbodiimide (2.06 g, 10 mmol) in pyridine (15 ml) added. The mixture was stirred at 4° C. for 4 days and diethyl ether (25 ml) added slowly. The mixture was cooled to 20° C. and the gummy solid filtered off. The material was triturated with chloroform (200 ml) overnight at room temperature and the residual solid filtered and recrystallised from (a) 35 ml H₂O, (b) 20 ml 25% v/v EtOH/H₂O. Yield after drying: 1.17 g (30%) m.p. 136°–140° C.

NMR (DMSO-⁶d)δ: 9.5. S. 4H, amidine (exch. D₂O). 8.03/7.50 Qt. 4H. amidinophenyl. 7.72. Irr. S. 2H. 2+6-H benzoyl. 6.75 D (J=9 Hz). 1H. 3-H benzoyl. 6.1 broad S. 2H exch. D₂O, amino. 2.13 S. 3H, methyl.

Analysis (duplicated): $C_{15}H_{16}N_3O_2Cl$ 1.5 H₂O requires: C, 54.13; H, 5.75; N, 12.62; Cl, 10.65. Found: C, 54.62, 54.54; H, 5.72, 5.62; N, 12.32, 12.34; Cl, 10.99, 10.70.

EXAMPLE 3

Preparation of 4-amidinophenyl-2'-amino-5'-methyl benzoate hydrochloride 5-methylanthranilic acid (7.56 g, 50 mmol) and 4-amidinophenol HCl (8.0 g, 50 mmol) were dissolved in dry pyridine (50 ml). Dicyclohexyl carbodiimide (11 g, 50 mmol) was added and the mixture stirred overnight at ambient temperature (c. 24° C.). Chloroform (50 ml) was added and the mixture stirred overnight at 40° C. Diethylether (150 ml) was added, the mixture stirred at 4° C. for 2 h and the gummy solid filtered off, washing with chloroform (1.0 liter). The solid was recrystallised from water (100 ml) and the filtrate precipitated by addition of saturated brine (20 ml) and standing overnight at 40° C. The solid was recrystallised from H₂O/brine (50/10 ml) and then water alone (20 ml). Yellow needles. m.p. 222°–223° C. (after drying). Yield: 1.95 g (11%).

NMR (DMSO⁶d)δ: 9.45. broad S. 4H. exch. D₂O, amidine. 7.45/7.95. Qt 4H, amidinophenyl. 7.72, S. 1H, benzoyl H. 7.20, DD. 1H, benzoyl-H, 6.76, D (J=10 Hz). 1H, benzoyl, H. 6.60. broad S 2H, exch. D₂O. amino. 2.16 S. 3H, methyl.

Analysis. $C_{15}H_{16}N_3O_2Cl$ requires: C, 58.91; H, 5.27; N, 13.74; Cl, 11.59. Found: C, 58.87; H, 5.10; N, 13.64; Cl, 11.34.

EXAMPLE 4

Preparation of 4-amidinophenyl-2'-amino-3'-methyl benzoate hydrochloride 3-methylanthranilic acid (3.02 g, 20 mmol) and 4-amidinophenol HCl (3.45 g, 20.4 mmol) were dissolved in dry pyridine (25 ml) and dicyclohexylcarbodiimine (4.2 g, 20.4 mmol) added. The mixture was stirred at 4° C. for 3 days. Diethyl ether (75 ml) was added and the mixture stirred for 24 h at 4° C. The solid was filtered and stirred with chloroform (800 ml) for 72 h at 4° C. Residual solid was recrystallised twice from water. Yield after drying: 1.00 g (10%) m.p. 125° C.

NMR (DMSO⁶d)δ: 9.52. S. 5H, amidine/H₂O. 7.46/8.03. Qt 4H, amidinophenyl H. 7.85, D. (J=9 Hz). 1H, 2-benzoyl H. 7.30, D. (J=7 Hz). 1H, 4-benzoyl H. 6.55, T 1H, 3-benzoyl H. 2.16 S 3H, methyl, also water peak.

Analysis: $C_{15}H_{16}ClN_3O_2H_2O$ requires: C, 55.64; H, 5.60; N, 12.97; Cl, 10.95. Found: C, 55.79; H, 5.46; N, 12.59; N, 12.59; Cl, 10.47.

EXAMPLE 5

Preparation of freeze dried 4-aminobenzoyl streptokinase plasminogen complex

Lys-plasminogen (Kabivitrum, 328 mg in 35 ml, 10 mM L-lysine pH 6.8) was mixed with 4-amidinophenyl 4'-aminobenzoic acid (Ditosylate salt, 2.6 ml, 20 mM in dimethylsulphoxide) and stirred for 2 min at 4° C. Streptokinase (Kabivitrum, 186 mg in 14.7 ml 30 mM sodium phosphate, 150 mM sodium glutamate pH 7.6) was added and the mixture stirred 1 h at 4° C. The solution was dialysed against two changes of 2 liters of L-lysine HCl, 1% w/v D-mannitol 1 mM 6-aminohexanoic acid pH 7.6 for 2 h (each change) at 4° C. The dialysed solution was diluted to 200 ml with dialysis buffer and human serum albumin (500 mg in 2.5 ml) added. The mixture was dispensed (10 ml aliquots) into 50 ml vials, frozen (acetone/solid CO₂) and freeze dried (shelf temperature $-20°$ C., pressure $4\times 10^{-2}$ torr, 30 h). Each vial contained a nominal 25 mg of complex.

EXAMPLE 6

Preparation of Freeze dried 2-aminobenzoyl streptokinase plasminogen activator complex 4-Amidinophenyl 2'-aminobenzoate 4-toluenesulphonate (30 ml of a 10 mM solution in dimethylsulphoxide) was added to human lys plasminogen (Kabivitrum, 11.4 mg, in 1.0 ml 10 mM L-lysine 6-H 6.8) and the solution mixed well. Streptokinase (4.98 mg in 0.5 ml 30 mM sodium phosphate, 150 mM sodium glutamate pH 7.6) was added and the mixture incubated 1 hour at 25° C. The sample was added to a small column of Sephadex ®G-25M (Pharmacia PD10 approx $1.5\times 10$ cm) equilibrated with 50 mM L-lysine, 5% w/v D-mannitol, 20 mM ammonium bicarbonate pH 7.8. The sample was applied (1.5 ml), and followed by 1.0 ml of the same buffer. Eluate was discarded and elution followed by 3.0 ml of the same buffer. Human serum albumin (0.3 ml of 200 mg/ml) was added to the eluate and the mixture dispensed in 0.2 ml aliquots into 2 ml vials. Vials were frozen (acetone/solid $CO_2$) and freeze dried for 5 hours at 0.05 torr and 22° C. Each vial contained a nominal 1 mg of complex. The deacylation rate constant of the complex was approximately $1.9\times 10^{-5}$ sec$^{-1}$ at pH 7.4, 37° C.

EXAMPLE 7

Preparation of Freeze Dried (5-methyl 2-aminobenzoyl)streptokinase plasminogen activator complex 4'-Amidinophenyl 5-methyl 2-aminobenzoic acid.HCl (75 μl of a 100 mm solution in dimethylsulphoxide) was mixed with human lys-plasminogen (Kabivitrum, 8.8 mg in 1.0 ml of 10 mm L-lysine pH 6.8) and streptokinase (Kabivitrum, 4.5 mg in 0.5 ml of 30 mm sodium phosphate, 150 mm sodium glutamate pH 7.6) added. The mixture was incubated for 75 mins at 25° C. and then gel filtered (as described in Example 6) into 3.5 ml of 1% w/v N-mannitol 25 mm L-lysine pH 7.8. The eluate was dispensed into $7\times 0.5$ ml aliquots and freeze-dried as described in Example 6. Each vial contained a nominal 1.9 mg of complex.

EXAMPLE 8

Preparation of Freeze Dried (3-methyl 4-aminobenzoyl) streptokinase plasminogen activator complex 4'-Amidinophenyl 3-methyl 4-aminobenzoic acid.HCl (28 μl of a 50 mm solution in dimethylsulphoxide) was mixed with human lys-plasminogen (Immuno AG, 6.86 mg in 1.0 ml 7.3 mm L-lysine, 0.21 mm 6-aminohexanoic acid pH 7.0) and streptokinase (Kabivitrum, 3.44 mg in 0.38 ml 30 mm sodium phosphate, 150 mm sodium glutamate pH 7.6) added. The mixture was incubated for 90 mins at 25° C. and gel filtered (as described in Example 6) into 3.2 ml of 0.5% w/v D-mannitol, 20 mm ammonium bicarbonate, 1.0 mm 6-aminohexanoic acid pH 7.4. The eluate was dispensed into $6\times 0.5$ ml aliquots and freeze dried as described in Example 6. Each vial contained a nominal 1.6 mg of complex.

BIOLOGICAL DATA

A. Clearance of fibrinolytic activity from the bloodstream of rabbits given acylated streptokinase plasminogen complexes

Method

Rabbits were sedated with Hypnorm (0.1 ml/kg) and both ears shaved. An initial blood sample (Po) was taken from a central ear artery to check for endogeneous activator activity. The compound (560 μg/kg) was injected rapidly (10–15 sec) into a marginal ear vein and a further blood sample was taken from the central ear artery of the contralateral ear within approximately 30 sec to obtain the initial activator level. Blood samples (1.8 ml into 2.0 ml syringes containing 0.2 ml, 3.8% citrate) were then taken at various time intervals.

Euglobulin fractions were prepared from the blood samples according to Austen DEG and Rhymes IL, 'A Laboratory manual of blood coagulation', (Blackwell, Oxford, 1975) p.80. The procedure both removes inhibitors and concentrates the activator. The fractions were then assayed on plasminogen-containing fibrin plates (human proteins). The plates were incubated for at least 18 h at 25° C. to allow time for complete deacylation and the areas of the lysis zones were calculated. The results are expressed as:

$$\% \text{ activity remaining} = \frac{(At - APo)}{(Ao - APo)} \times 100$$

The calculated half-life for the lytic activity is obtained by plotting $$-\log_e \frac{(At - APo)}{(Ao - APo)} \text{ vs time}$$

and reading off the time at which $$\frac{(At - APo)}{(Ao - APo)} = 0.5.$$

The results are shown in FIG. 1.

Results

Unmodified streptokinase plasminogen activator complex was cleared rapidly with an apparent half-life of about 11 min. The 4 guanidinobenzoyl SK.plasminogen complex was removed more slowly (t½282 min) but the lytic activity derived from 4-aminobenzoyl SK.plasminogen was not significantly cleared over the 6 h experimental period.

B. Effect on circulating $\alpha_2$-antiplasmin levels in rabbits of injection of (4-guanidinobenzoyl)- and (4-aminobenzoyl)-streptokinase plasminogen complex

Method

Rabbits were given intravenous injections of agents (280 μg/kg) in normal saline (2.0 ml). Blood samples (2.0 ml) were taken at 60 min intervals and centrifuged to obtain platelet-poor plasma. $\alpha_2$-Antiplasmin (fast antiplasmin) was determined in plasma according to the method of Friberger P. et al. Haemostasis 7, 138–145 (1978) using a standard plasmin of known molarity. $\alpha_2$-antiplasmin is therefore expressed in molarity of functional protin.

Results

The effect of 4-aminobenzoyl SK.plasminogen on $\alpha_2$-antiplasmin level in 2 animals and the corresponding effect of 4guanidinobenzoyl SK.plasminogen in 5 animals are shown in FIG. 2. A drop in $\alpha_2$-antiplasmin of 40–50% over 4–5 hour was observed following administration of the latter compound but there was no significant change in $\alpha_2$-antiplasmin after administration of 4-aminobenzoyl SK.plasminogen. A drop in $\alpha_2$-antiplasmin implies a systemic activation of plasminogen and may be correlated with increased haemorrhagic risk. The same dose of both agents gave significant clot lysis when tested in the rabbit thrombosis model disclosed in European Patent Application, Published No. 9879 (See Section C). The compounds are therefore both thrombolytic agents but the 4-aminobenzoyl derivative has the lesser effect on haemostasis.

C. Thrombolytic activity of (4-aminobenzoyl)-streptokinase plasminogen complex in a rabbit model of venous thrombosis

Method

The rabbit model of venous thrombosis was that described in Thrombosis and Haemostasis 46 (2), 528–594, 1981 and disclosed in European Patent Application, Published No. 9879. Enzyme was administered in 2 ml of sterile saline over 2 min. Most experiments were performed over 5 h but in some cases the experimental period was extended to 10 h.

Results

The lysis induced by various doses of the acyl enzyme is given in the table.

TABLE

Percent Radiochemical Thrombolysis produced by (4-aminobenzoyl) streptokinase plasminogen complex

| Dose ($\mu$g/kg) | Batch No. | No of animals | Duration of Experiments | % Lysis $\pm$ SEM |
|---|---|---|---|---|
| Controls (saline) | — | 8 | 5 h | 3 $\pm$ 1 |
| 70 | DB078 | 7 | 5 h | 20.2 $\pm$ 4 |
| 70 | DB083 | 4 | 5 h | 24.9 $\pm$ 5 |
| 70 | DB078 | 8 | 10 h | 40.8 $\pm$ 6.6* |
| 140 | DB078 | 5 | 5 h | 31.0 $\pm$ 7.7 |
| 280 | DB078 | 4 | 5 h | 45.0 $\pm$ 8 |
| 280 | DB083 | 4 | 5 h | 41.6 $\pm$ 4 |
| 840 | DB078 | 3 | 5 h | 63.1 $\pm$ 10 |

*Significantly different from 5 h group at same dose ($P < 0.05$)

CONCLUSIONS

The results indicate that the 4-aminobenzoyl streptokinase plasminogen can produce dose-related thrombosis in an animal model of thrombosis. The fact that the end lysis at a fixed dose was significantly increased when the experimental period was extended from 5 to 10 h suggests that this substance has a duration of effective fibrinolytic activity in vivo which exceeds 5 h.

I claim:

1. A derivative of streptokinase-human plasminogen activator complex in which the active catalytic site essential for fibrinolytic activity is blocked by a 2- or 4-aminobenzoyl group which is optionally substituted in the aromatic ring by an electron donating moiety, the group being removable by hydrolysis such that the first order rate constant for hydrolysis of the derivative is in the range $0.7 \times 10^{-5}$ sec$^{-1}$ to $2.5 \times 10^{-5}$ sec$^{-1}$ in isotonic aqueous media at pH 7.4 at 37° C.

2. A derivative according to claim 1, in which the first order rate constant is from $1 \times 10^{-5}$ sec$^{-1}$ to $2 \times 10^{-5}$ sec$^{-1}$.

3. A derivative according to claim 1, in which the aminobenzoyl group is substituted by a $C_{1-6}$ alkyl, $C_{1-6}$ alkoxy or $C_{1-6}$ alkenyl group.

4. A derivative according to claim 1, selected from 4-aminobenzoyl streptokinase plasminogen activator complex, 2-aminobenzoyl streptokinase plasminogen activator complex, 4-amino-3-methylbenzoyl streptokinase plasminogen activator complex, or 2-amino-3-methylbenzoyl streptokinase plasminogen activator complex.

5. A process for preparing a derivative according to claim 1, which comprises reacting streptokinase plasminogen activator complex with a blocking agent of the formula in which A is a locating group which locates the agent in the catalytic site, and B is a 2- or 4-aminobenzoyl group optionally substituted in the aromatic ring by an electron donating moiety.

6. A process according to claim 5, in which the group A is a 4-amidinophenyl or 4-acetamidinophenyl group.

7. A pharmaceutical composition useful for treating venous thrombosis in humans which comprises a therapeutically effective amount of a derivative of streptokinase-human plasminogen activator complex in which the active catalytic site essential for fibrinolytic activity is blocked by a 2- or 4-aminobenzoyl group which is optionally substituted in the aromatic ring by an electron donating moiety, the group being removable by hydrolysis such that the first order rate constant for hydrolysis of the derivative is in the range $0.7 \times 10^{-5}$ sec$^{-1}$ to $2.5 \times 10^{-5}$ sec$^{-1}$ in isotonic aqueous media at pH 7.4 at 37° C., in combination with a pharmaceutically acceptable carrier.

8. A composition according to claim 7 in which the first order rate constant is from $1 \times 10^{-5}$ sec$^{-1}$ to $2 \times 10^{-5}$ sec$^{-1}$.

9. A composition according to claim 7 in which the aminobenzoyl group is substituted by a $C_{1-6}$ alkyl, $C_{1-6}$ alkoxy or $C_{1-6}$ alkenyl group.

10. A composition according to claim 7 wherein the derivative is selected from 4-aminobenzoyl streptokinase plasminogen activator complex, 2-aminobenzoyl streptokinase plasminogen activator complex, 4-amino-3-methylbenzoyl streptokinase plasminogen activator complex, or 2-amino-3-methylbenzoyl streptokinase plasminogen activator complex.

11. A composition according to claim 7 in intravenous administration form.

12. A method for treating venous thrombosis in humans which comprises administering to a human in need thereof a therapeutically effective amount of a derivative of streptokinase-human plasminogen activator complex in which the active catalytic site essential for fibrinolytic activity is blocked by a 2- or 4-aminobenzoyl group which is optionally substituted in the aromatic ring by an electron donating moiety, the group being removable by hydrolysis such that the first order rate constant for hydrolysis of the derivative is in the range $0.7 \times 10^{-5}$ sec$^{-1}$ to $2.5 \times 10^{-5}$ sec$^{-1}$ in isotonic aqueous media at pH 7.4 at 37° C., in combination with a pharmaceutically acceptable carrier.

13. A method according to claim 12 in which the first order rate constant is from $1 \times 10^{-5}$ sec$^{-1}$ to $2 \times 10^{-5}$ sec$^{-1}$.

14. A method according to claim 12 in which the aminobenzoyl group is substituted by a $C_{1-6}$ alkyl, $C_{1-6}$ alkoxy or $C_{1-6}$ alkenyl group.

15. A method according to claim 12 wherein the derivative is selected from 4-aminobenzoyl streptokinase plasminogen activator complex, 2-aminobenzoyl streptokinase plasminogen activator complex, 4-amino-3-methylbenzoyl streptokinase plasminogen activator complex, or 2-amino-3-methylbenzoyl streptokinase plasminogen activator complex.

16. A method according to claim 12 wherein the administration is intravenous.

* * * * *